(12) United States Patent
Mann et al.

(10) Patent No.: US 7,235,377 B2
(45) Date of Patent: Jun. 26, 2007

(54) GLOBAL TEST OF THE HEMOSTATIC SYSTEM

(75) Inventors: Kenneth G. Mann, Grand Isle, VT (US); Kathleen Brummel, Waterbury Center, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 10/865,608

(22) Filed: Jun. 9, 2004

(65) Prior Publication Data

US 2005/0118653 A1 Jun. 2, 2005

Related U.S. Application Data

(60) Provisional application No. 60/477,213, filed on Jun. 9, 2003.

(51) Int. Cl.
*C12Q 1/56* (2006.01)
(52) U.S. Cl. .......................... 435/13; 436/69
(58) Field of Classification Search .............. 435/13, 435/23; 436/69
See application file for complete search history.

(56) References Cited

U.S. PATENT DOCUMENTS 6,403,381 B1 * 6/2002 Mann et al. ................. 436/69
6,645,768 B1 * 11/2003 Tejidor et al. ................. 436/8
2003/0064414 A1 * 4/2003 Benecky et al. .......... 435/7.21

FOREIGN PATENT DOCUMENTS

WO   WO 02/079375 A1 * 10/2002

* cited by examiner

*Primary Examiner*—Ralph Gitomer
(74) *Attorney, Agent, or Firm*—Edwards Angell Palmer & Dodge LLP; David G. Conlin; Dwight D. Kim (57) ABSTRACT

The instant invention describes a method for establishing the hemostatic competence of blood, wherein the steps of the method include obtaining a blood sample from a subject, contacting the blood sample with an effective amount of tissue factor under conditions conducive to coagulating blood; and detecting the amount of thrombin in the blood sample at a pre-determined time point. The invention also describes a method for testing the capacity of an individual subject to produce thrombin, wherein the steps of the method include obtaining a blood sample from the subject; contacting the blood sample with an effective amount of tissue factor under conditions conducive to coagulating blood; and detecting the amount of thrombin produced in the blood sample at a pre-determined time point.

28 Claims, 5 Drawing Sheets

GLOBAL TEST OF THE HEMOSTATIC SYSTEM

RELATED APPLICATIONS

This application claims priority to U.S. Provisional Application 60/477,213 filed Jun. 9, 2003, which is herein incorporated by reference in its entirety.

STATEMENT OF GOVERNMENT SUPPORT

Funding for this invention was provided in part by the Government of the United States of America, through Grant No. HL07594, by the National Institutes of Health. The Government has certain rights in this invention.

FIELD OF THE INVENTION

This invention generally relates to methods for measuring coagulation of blood and blood products. More specifically, this invention provides methods and systems for assaying the capacity to generate thrombin and to monitor the hemostatic competence of blood.

BACKGROUND

Hemostasis involves control of bleeding and is typically viewed as a cascade of processes that help regulate blood coagulation. Central to the hemostasis process is thrombin generation. Thrombin is a proteolytic enzyme, which is generated in the blood following activation of the coagulation system as a result of proteolysis of prothrombin. It facilitates the clotting of blood by activating fibrinogen and releasing the fibrinopeptides A and B to form fibrin. Thrombin has many functions extending from coagulation activator and inhibitor to cellular regulator. Thrombin generation, essential in the hemostatic process and the maintenance of vascular integrity is also associated with vasoocclusive events leading to heart attacks, stroke, pulmonary embolism and venous thrombosis.

The physiologic pathway for thrombin generation occurs when the vascular system is perturbed. A perturbation is thought to facilitate the expression of tissue factor which binds circulating factor VIIa and forms the extrinsic tenase complex. During an initiation phase of this process, factor IX and factor X are converted to the serine proteases factor IXa and factor Xa, and the initial factor Xa formed, activates prothrombin to thrombin. See e.g., Mann, K. G. et al. (1990) *Blood* 76: 1; Mann, K. G. et al. (1992), supra.

Thrombin activates platelets, fibrinogen, factor XIII and the procofactors factor VIII and factor V providing the membrane receptors, factor VIIIa and factor Va. The membrane bound cofactors then are believed to bind factor IXa (the intrinsic tenase) and factor Xa (prothrombinase) to provide the major products of the hemostatic process, during a propagation phase of thrombin generation. As thrombin is being generated it is also down regulated by the stoichiometric inhibitors antithrombin III and tissue factor pathway inhibitor, and in the vasculature, the dynamic thrombin—thrombomodulin—protein C system.

On average, in tissue factor triggered whole blood in vitro, it is thought that approximately 60% of prothrombin is activated to thrombin, of which approximately 3% (10-20 nM thrombin-antithrombin III, TAT) produced during the initiation phase is required to clot whole blood. Following the visual clot time, 97% of the thrombin is generated during the propagation phase. In healthy individuals, the initiation phase duration and the activation of procoagulants during the propagation phase is believed to be fairly constant.

In hemophilia A the initiation phase is thought to be delayed, but the major defect observed is a severely attenuated propagation phase. The propagation phase is also depressed for individuals on coumadin therapy, in thrombocytopenic individuals, and by anti-platelet glycoprotein IIbIIIa therapies. These observations suggest that the combination of the generation of a sufficient level of thrombin (propagation phase), in a timely fashion (initiation phase), is of importance.

A thrombin assay that can measure the capacity of an individual to produce thrombin over time is needed. Such an assay would find use, for instance, in monitoring healthy individuals for variations in their thrombin levels potentially signifiying a change in hemostatis; as well the hemostatic competence of patients with hemophilia, individuals on anticoagulant therapy, thrombocytopenic individuals, and with patients on anti-platelet therapies, among other uses.

U.S. Pat. No. 6,403,381 to Mann et al. describes methods for inhibiting blood clotting which include adding corn trypsin inhibitor in an amount sufficient to inhibit blood clotting, in order to permit clotting assays featuring prolonged clotting times. This patent also discloses clotting assays using whole or minimally altered blood.

SUMMARY OF THE INVENTION

The invention generally relates to methods for measuring coagulation of blood and blood products. It is a tissue factor based assay of thrombin-antithrombin III generation and it can be used in looking at bleeding states, thrombotic states and non-diseased states. In one embodiment, the invention provides a method for establishing hemostatic competence of blood that includes at least one and preferably all of the following steps: obtaining a blood sample from the subject, contacting the blood sample with an effective amount of tissue factor under conditions conducive to coagulating blood; and detecting the amount of thrombin produced in the blood sample at a single pre-determined time point.

In another embodiment this invention provides a method for establishing hemostatic competence of blood that includes preparing an evacuated blood collection tube containing a lyophilized preparation of corn trypsin inhibitor (CTI) and relipidated tissue factor for use in direct phlebotomy. The tube can also serve as the assay tube for the incubation period as well as the centrifugation tube for serum separation.

In another embodiment this invention provides a method for establishing the hemostatic competence of blood by a plasma based assay that includes collecting blood into an evacuated blood collection tube containing sodium citrate and contact pathway inhibitors. The plasma derived form this tube can then be assayed in a modified tissue factor (TF) initiated thrombin generation assay or stored frozen for subsequent analysis.

The invention provides many advantages. For instance, it is grounded in the discovery that there exists variation in tissue factor initiated thrombin production within groups, but thrombin production in an individual does not significantly vary. This invention measures a large spread in thrombin production for populations of individuals, but a tight spread for individuals. This makes the present invention an excellent assay in several respects. For instance, variations in thrombin production in an individual can be reliably measured and monitored, and temporal changes in the hemostatic competence in an individual detected.

Thus, the invention provides an assay method that is capable of measuring individual variations within a population. In a healthy population, a wide range of thrombin production in a tissue factor initiated reaction by this invention is observed. The assay can measure individual variation within a population. However, the demonstration that individual variance is low, shows that this invention can also identify changes or trends in the ability of an individual to produce thrombin over time. The assay can therefore detect changes in the hemostatic competence of an individual over time. These features provide useful advantages including allowing the method to be a reliable and reproducible indicator of hemostatic blood competence.

Practice of the invention provides other advantages. For instance, thrombin is generated in a native environment with no dilution, anticoagulation, temperature change, or detecting substrate to alter the outcome, thereby maximizing assay sensitivity and selectivity, for example.

Additionally, unlike other assays, this invention provides for thrombin sampling at a specific point in time. This provides the advantage that an individual response at a given sampling time can be compared over a period of months or years. This invention can therefore measure changes over time in an individual's hemostatic competence.

The invention also provides a system for measuring an individual's hemostatic competence. In one embodiment, the system includes at least one of and preferably all of a reaction vessel, corn trypsin inhibitor or an active fragment thereof, and tissue factor. In a preferred example of the invention, the system also includes a detector for measuring the amount of thrombin produced in the reaction vessel at a pre-determined time, and a device for accepting input from a detector and outputting data indicating the amount of thrombin present in the blood sample.

Preferred use of the system is intended to carry out the methods of this invention. The individual components can be arranged or packaged in any convenient way provided the intended results are achieved. The individual elements of the system need not be physically related to each other, or connected, in any particular way. It is also not necessary for all of the components to be packaged or arranged in any particular way, in the same carton, box, etc. A preferred system is discussed in more detail below. Additional examples and advantages of the invention are also discussed below.

DETAILED DESCRIPTION OF THE INVENTION

Figure 5:
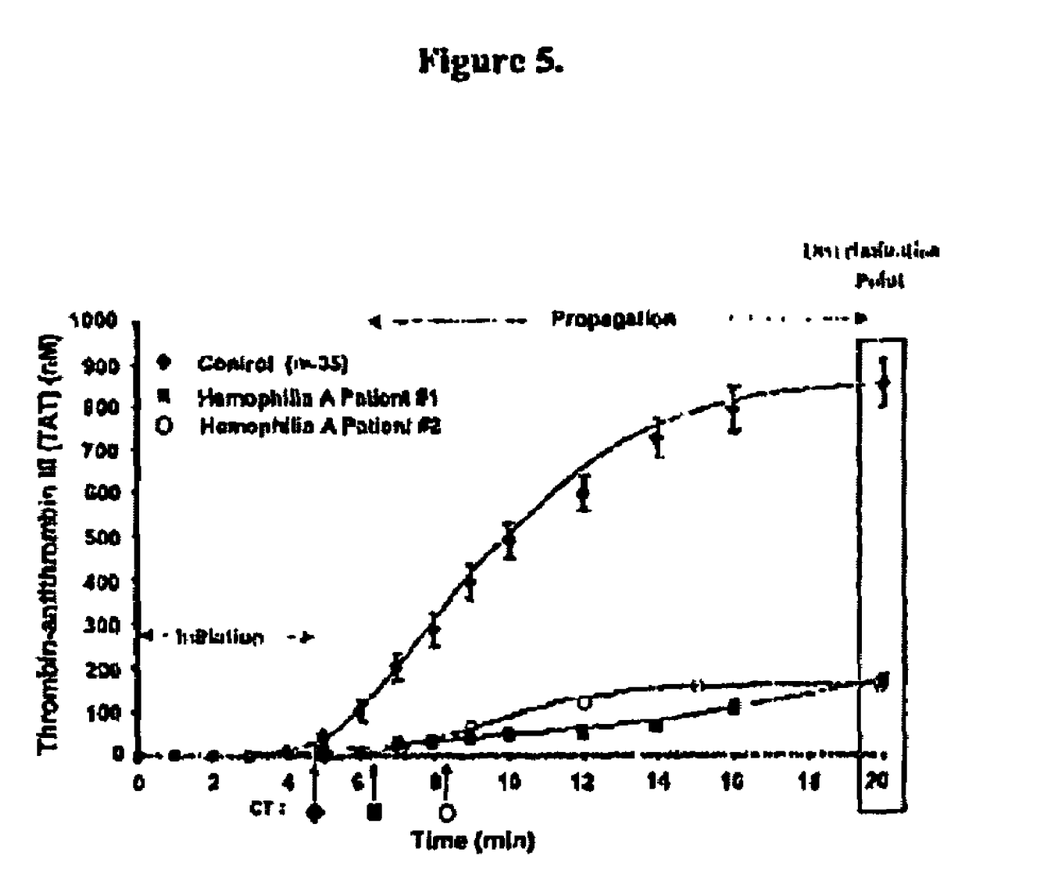
FIG. 5 illustrates the importance of determining thrombin generation utilizing this para vivo whole blood model. In hemophilia A individuals, the initiation phase is thought to be delayed (CT), but the major defect observed is a severely attenuated propagation phase. The propagation phase is also depressed for individuals on coumadin therapy, in thrombocytopenic individuals, and by anti-platelet glycoprotein IIbIIIa therapies.

The graph shown below illustrates the importance of determining thrombin generation utilizing this para vivo whole blood model. When thirty-five healthy individuals were studied, the initiation phase duration (clot time, CT) and the propagation phase of thrombin appear to be fairly constant. See also Brummel K E, Paradis S G, Butenas S, Mann K G. Thrombin functions during tissue factor-induced blood coagulation. Blood. 2002;100:148-152. In hemophilia A individuals, the initiation phase is thought to be delayed (CT), but the major defect observed is a severely attenuated propagation phase. The propagation phase is also depressed for individuals on coumadin therapy, in thrombocytopenic individuals, and by anti-platelet glycoprotein IIbIIIa therapies. These observations suggest that the combination of the generation of a sufficient level of thrombin (propagation phase) in a timely fashion is of importance. (See FIG. 5).

As discussed, in one embodiment the invention is a method for testing the capacity of an individual to produce thrombin. A preferred method involves isolating blood from a subject, and then inhibiting contact coagulation in the isolated blood. The blood sample is contacted with an effective amount of tissue factor under conditions conducive to producing thrombin, and then the amount of thrombin produced at a particular time is detected. The elements of this invention can be performed in any convenient manner or order.

In another embodiment this invention provides a method for establishing hemostatic competence of blood that includes preparing an evacuated blood collection tube containing a lyophilized preparation of corn trypsin inhibitor (CTI) and relipidated tissue factor for use in direct phlebotomy. The tube can also serve as the assay tube for the incubation period as well as the centrifugation tube for serum separation.

The blood collection tubes can be used to optimize the actual assay protocol to make the assay more user friendly and with better reproducibility. The general procedure for performing the tissue factor initiated thrombin generation assay utilizing these tubes involves the following steps: 1) Drawing blood into a tube containing relipidated tissue factor/inhibitor cocktail, 2) Rocking the tube @ 37° C. for 20 minutes, 3) Addition of an inhibitor cocktail to quench the reaction, and 4) Assaying serum for TAT.

In another embodiment this invention provides a method for establishing the hemostatic competence of blood by a plasma based assay that includes collecting blood into an evacuated blood collection tube containing sodium citrate and contact pathway inhibitors. The plasma derived form this tube can then be assayed in a modified tissue factor initiated thrombin generation assay or stored frozen for subsequent analysis.

There are a number of advantages for a plasma based assay. A plasma-based assay might be easier to perform at the level of a clinical laboratory since plasma samples could be stored frozen and assayed when most convenient. Another advantage would be the ability to prepare stable normal and abnormal control plasmas for quality control purposes.

The data in Table 1 was obtained by a preferred embodiment of the present invention. Table 1 shows data for 13 healthy subjects with thrombin measurements taken over a period of 6 months. Table 1 shows that the mean individual variance is low and that the mean variance for the group $CV_g$ is high.

TABLE 1

TAT levels after 20 minutes.

| Subject | Month 1 | Month 2 | Month 3 | Month 4 | Month 5 | Month 6 | Mean ± SD |
|---|---|---|---|---|---|---|---|
| 1 | 487.6 | 449.6 | 422.7 | 317.3 | 386.9 | 335.9 | 400 ± 65.9 |
| 2 | 529.4 | N/D | 572.7 | N/D | 478.4 | N/D | 526.8 ± 47.2 |
| 3 | 723.5 | 718.0 | 547.3 | 575.1 | 555.7 | 658.2 | 629.6 ± 80.8 |
| 4 | 470.2 | 404.3 | 443.1 | 437.6 | 358.0 | 450.4 | 427.2 ± 40.2 |
| 5 | 314.7 | 352.4 | 312.2 | 284.5 | 305.9 | 304.5 | 312.4 ± 22.3 |
| 6 | 565.7 | 532.0 | 758.8 | N/D | 774.7 | 498.0 | 625.8 ± 131.0 |
| 7 | 524.5 | 436.7 | 394.9 | 355.1 | 29.2 | 423.1 | 427.2 ± 56.2 |
| 8 | N/D | 407.3 | 559.0 | 366.9 | 478.2 | 499.2 | 462.1 ± 75.9 |
| 9 | 391.0 | 436.5 | 387.8 | 430.2 | N/D | 362.4 | 401.6 ± 31.1 |
| 10 | 288.0 | 278.0 | 244.9 | 280.8 | 246.5 | 285.7 | 270.6 ± 19.6 |
| 11 | 437.6 | 280 | 259.6 | 334.7 | 308.2 | 283.1 | 317.2 ± 64.4 |
| 12 | 362.4 | 364.3 | 360.2 | 406.7 | 387.8 | 436.5 | 386.3 ± 30.6 |

Table 1 shows that this invention provides an excellent diagnostic test. The invention can detect the range of variation present in groups but also shows that the variation for an individual is small. This invention can therefore reliably measure changes in hemostatic competence over time in an individual.

In one preferred embodiment, blood would first be taken from a patient. This can be done at the site of the assay, or elsewhere with the blood sample then being transported to the entity carrying out the remaining steps of the assay. The sampled blood is then added to a reaction vessel with corn trypsin inhibitor and tissue factor already present in the vessel. The vessel is then rocked at about 37° C. and quenched with buffers at a pre-determined time. Optionally, the sample can be stored at low temperature for further analysis at a later time. The thrombin produced is then detected by a suitable detection method.

The reaction vessel is any convenient vessel in which the blood sample, inhibitor and tissue factor can be conveniently mixed. Preferably, the reaction vessel is a glass test tube of sufficient size to accommodate all of the components. Blood can be isolated from the subject by any suitable means. Blood isolation from the subject need not be done at the same site as the assay, or be performed by the same entity. A preferred method would be by venipuncture.

The contact coagulation that occurs when blood contacts the glass of a test tube is inhibited by any suitable method. Corn trypsin inhibitor is highly preferred, as described in U.S. Pat. No. 6,403,381, which is herein incorporated by reference. The corn trypsin inhibitor can be used alone, or in combination with other anticoagulants. Corn trypsin inhibitor minimizes blood coagulation in vitro, and obviates sources of error and inconsistency in blood coagulation measurements.

Tissue factor preparation can be accomplished through any suitable method. A preferred method is to use phospho-lipid-tissue factor relipidated in PCPS (1:2000 protein/lipid). This method is described in various publications including, Rand et al., "Blood clotting in minimally altered whole blood." Blood. 1996;88:3432-3445; Cawthern et al., "Blood coagulation in hemophilia A and hemophilia C," Blood 1998;91:4581-4592; and Brummel et al., "An integrated study of fibrinogen during blood coagulation. J. Biol. Chem. 1999;274:22862-22870. A sufficient amount of tissue factor is used to ensure that enough thrombin is generated throughout the population to be studied.

The assay is performed at any suitable temperature. Preferably the assay is done at between about 0 and about 100 degrees Celcius. More preferably between about 25 and about 50 degrees Celcius. Most preferably at between about 30 and about 40 degrees Celcius.

Quenching is done by any suitable method but is preferably done with the use of inhibitors. A preferred method is with EDTA and Benzamide-HCl in HBS, at a pH of about 7.4, plus FPRck in HCl, freshly prepared. An amount of inhibitor is used that will stop thrombin production in the blood. The quenching is preferably done at a time after thrombin production is complete. Preferably, the quenching is done at a time that is less than about 100 minutes. More preferably between about 0.5 minutes and about 50 minutes. Most preferably between about 8 minutes and about 25 minutes. Clot times can be determined visually. Samples can be optionally stored at low temperature prior to further analysis.

Thrombin is detected by any suitable method. A preferred method is through an immunological assay. Immunological assays are techniques for the measurement of biochemical substances that involve adding to a sample a limited amount of a specific antibody. The fraction of antigen combining with the substance to be analyzed for is then estimated using some form of an indicator.

A preferred method is through the use of a commercial enzyme linked immunosorbant assay made by Behring (Westwood). A standard curve is generated using concentration standards run in duplicate. Whole blood samples are then diluted and also run in duplicate. An optical density reading is then obtained.

Preferably, the optical density reading is obtained on a TMax microtiter plate reader equipped with SOFTMAX version 2.0 software (Molecular Devices, Menlo Park, Calif.). Concentration results are then obtained using a comparison to absorbance at 490 nm and fit to a four-parameter equation $(y=(A-D)/(1+(x/C)^B)+D)$. Parameters A-D are determined by the SOFTMAX software from the generated standard curve.

Other detection methods that can be used with this invention would include radio immunological assay and western blot analysis, among others.

Further Details of Methods and Materials

Recombinant human tissue factor can be obtained from LifeScan, Inc. Milpitas, Calif. Recombinant human tissue factor can also be commercially obtained from American Diagnostica, Inc. (Greenwich, Conn.).

Phosphatidylcholine (PC), Phosphatidylseine (PS), Phosphatidylethanolamine (PE), and Phosphatidylglycerol (PG) can be purchased from Avanti Polar Lipids, Alabaster, Ala. Phospholipid vesicles can be composed of either 75:25 PC:PS or a blend of PC:PS:PG:PE and perform well in the whole blood thrombin generation assay. Vesicles can be formed utilizing a process involving solubilizing the lipid blend in the presence of Zwiterionic detergent that is subsequently removed chromatographically.

The method is scaleable and is particularly well suited to large-scale manufacturing. Phospholipid vesicles are prepared by a previously reported sonication method described in Barenholz Y, Gibbes D, Litman B J, Goll J, Thompson T E, Carlson R D. A simple method for the preparation of homogeneous phospholipid vesicles. Biochemistry. 1977; 16:2806-2810. In all cases the overall phospholipid concentration will be assessed by determination of inorganic phosphate as described in Higgins D. L., Mann K. G., The interaction of bovine factor V and factor V-derived peptides with phospholipid vesicles. J. Biol. Chem. 1983; 258:6503-6508.

Several methods can be used to incorporate tissue factor into the phospholipid vesicles. In one method, predetermined quantities of tissue factor and phospholipids are co-solubilized with zwiterionic detergents. Vesicle formation is promoted by chromatographic removal of detergent followed by filtration. Another method utilizes low concentrations of TWEEN-80 to facilitate incorporation of tissue factor into preformed phospholipid vesicles. See Lawson J H, Krishnaswamy S, Butenas S, Mann K G. Extrinsic pathway proteolytic activity. Methods Enzymol. 1993;222: 177-195. The first method should yield vesicles with 50% of the tissue factor effectively oriented in the lipid bilayer whereas the second method should have 100% of the tissue factor oriented such that the factor VIIa binding site is on the outside of the membrane.

Although a prothrombin time reagent prepared by the second method and composed of 5 nM TF, 10 mM phosphatidyl choline/phosphatidly serine (75:25, PCPS) yields acceptable results, the ratio of tissue factor to phospholipid can be varied to optimize thrombin generation, and reagent stability. In addition to the reagents described above, a commercially available thromboplastin reagent Recombi-PlasTin (Beckman Coulter) can be used as a source of relipidated tissue factor.

Corn trypsin inhibitor, human antithrombin III, phe-pro-arg-chloromethylketone, and an inhibitory anti-factor XI monoclonal antibody, can also be obtained commercially. Aprotinin and Pefabloc-SC, can be obtained commercially and can be purchased, for example, from Centerchem, Inc., Stamford, Conn. Heparin can be obtained commercially and can be purchased, for example, from the pharmacy at Fletcher Allen Healthcare, Burlington, Vt. Citric acid, sodium citrate, EDTA and other miscellaneous chemicals can also be purchased from various manufacturers.

Glass tubes and stoppers can be purchased commercially, for example from Tyco, Inc., (Mansfield, Mass.) and plastic blood collection tubes can also be obtained commercially, for example, from Greiner Bio-One, Longwood, Fla. or Becton Dickson, (Franklin Lakes, N.J.).

The functional activity of relipidated tissue factor preparations can be quantitated using a tissue factor assay which exploits the 200 fold rate increase of factor VIIa mediated hydrolysis of the fluorogenic substrate D-FPR-ANSNH-C4H9:2HCl, in the presence of tissue factor (ref. Haemetologic Technologies U.S. Pat. No. 5,399,487).

Normal citrated human plasma can be purchased from Seraplex, Inc., Duarte, Calif. Seraplex, Inc., operates an FDA licensed plasma distribution facility. No donor identification is generally made available. Normal pooled plasma can be prepared from a minimum of 20 donor units of fresh frozen plasma. The normal pooled plasma (neat or augmented with inhibitors) is generally aliquoted and stored frozen at less than about $-40°$ C. Some assays use blood obtained by phlebotomy from volunteer donors.

The incubation time established for the traditional liquid format assay is 20 minutes with a broad plateau for normal donors in the range of 15-30 minutes. A shorter assay time with a broad plateau can also be used. Mixing can also be done by manual inversion, the tubes are placed at $37°$ C. for 20 minutes. The ability to leave the tubes stationary during the incubation period eliminates requirements for mixing equipment. The preferred assay is performed at about $37°$ C., although a temperature range of about $15\text{-}45°$ C. is acceptable.

This invention also encompasses an efficient quenching formulation suitable for single addition that is stable (freeze dried) and cost effective. In addition to examining the effect of varying the concentrations and order of addition of these inhibitors, a select group of alternative inhibitors are also used.

The most common anticoagulants used in blood collection tubes are the metal ion chelating agents, EDTA and citrate. A preferred quenching protocol calls for addition of EDTA to a final concentration of 25 mM in whole blood, which is approximately 5-fold higher than the concentration typically used as an anticoagulant. In addition to this inhibitor 10-20 mM citric acid is also used. One advantage citric acid has over EDTA in this system is that stock solutions can be formatted over a wide range of pH (2.5-10) allowing greater flexibility in relation to the stability of the other components in the inhibitor cocktail. This is of particular importance with regard to FPRck, EGRck and Pefabloc-SC, which are labile at neutral pH.

Heparin is also a commonly used anticoagulant in blood collection tubes and can be used. It primarily functions as a potent inhibitor of factor Xa and thrombin by promoting inhibitory complexes with ATIII, the endpoint of our assay. Heparin is very stable, cost effective and available "off the shelf" in pharmaceutical grade preparations. We titrate heparin concentrations in whole blood around a target value of 10 units/ml.

The endpoint of the assay relies on the formation of an inhibitory complex between newly generated thrombin and endogenous antithrombin III. It is possible that in some circumstances, insufficient endogenous levels of antithrombin III may adversely effect the endpoint measurement. Thus the serum sample can be augmented at the end of the incubation period with 0-2 mM antithrombin III. It is generally important to add the antithrombin III at the end of the incubation period so as not to influence the overall rate of thrombin generation.

Pefabloc SC is a potent broad-spectrum irreversible serine protease inhibitor that can also be used. It is readily water soluble, and more stable at neutral pH than similar compounds in its class. A concentration of 0-25 mM is present. These inhibitors can be used in combination with each other. Preferably, the inhibitor cocktail would have no more than three components. The inhibitor cocktails can also be lyophilized.

For convenience, it is desirable to store the quenched serum sample generated by incubation with relipidated tissue factor for subsequent assay in the TAT ELISA. Since a typical assay requires the serum sample to be diluted 1:1000 prior to performing the TAT ELISA, 1 ml of serum is generally enough to be saved for subsequent testing.

The ratio of tissue factor:phospholipid as well as the relative proportions of PC, PS, phosphatidylethanolamine (PE) and phosphatidylglycerol (PG) in the phospholipid blend can be varied. The formulations can be co-lyophillized with CTI into evacuated blood collection tubes. Preferred formulations maximizes thrombin generation at the lowest possible TF concentration.

A commercially available PT reagent composed of relipidated full length recombinant human tissue factor is an alternate source of relipidated TF. This preparation is supplied as a freeze-dried powder, which is readily soluble in water. Vials of this material are reconstituted with a minimal volume of water and then assayed for phospholipid content (by inorganic phosphate assay, Davey M G,). Actions of thrombin and other coagulant and proteolytic enzymes on blood platelets. Nature. 1967;216:857-858.) and functional tissue factor activity as described above. The material can be formulated with excipients and co-lyophilized with CTI into evacuated blood collection tubes. The formulations can be co-lyophilized with CTI into evacuated blood collection tubes.

Phospholipids can also be purchased pre-blended to specification by Avanti Polar Lipids (Alabaster Ala.). The over phospholipid concentration in the formulation is quantitated by determining the concentration of inorganic phosphate by an established protocol. See Barenholz Y, Gibbes D, Litman B J, Goll J, Thompson T E, Carlson R D. A simple method for the preparation of homogeneous phospholipid vesicles. Biochemistry. 1977;16:2806-2810. The ratios of the individual phospholipids components (PC, PE, PS, PG) are determined by HPLC analysis.

The functionality (and therefore the orientation) of the relipidated tissue factor can be assessed by several methods. One method utilizes the ability of the factor VIIa/tissue factor complex to convert factor X to factor Xa 44. See Fay P J. Subunit structure of thrombin-activated human factor VIIIa. Biochim. Biophys. Acta. 1988;952:181-190. Dilutions of relipidated tissue factor are incubated with fixed concentrations of factors VIIa and X in a buffer system composed of 20 mM HEPES, 150 mM NaCl, 2 mM CaCl2, pH 7.4. The conversion of factor X to factor Xa is quantitated by monitoring the hydrolysis of the chromogenic substrate Spectrozyme Xa by factor Xa at 405 nm in a Vmax (molecular Devices) kinetic microplate reader. In this system, only the activity of TF effectively oriented in the phospholipids vesicle is detected.

A second method involves assessing the ability of the relipidated tissue factor to function as an initiator in a standard plasma based clotting assay on the MLA 1400 coagulation analyzer. Dilutions of relipidated tissue factor will be made in the above buffer and substituted for the PT reagent in a standard PT assay format. Three levels of reference plasma (Hemoliance Plasma Coagulation Controls I-III) are assayed in this system and compared to assays utilizing Hemoliance RecombiPlastTin (ISI=1.0) as the PT reagent. The slope of the line generated from a plot of the PT times obtained with RecombiPlasTin versus our PT reagent is used to calculate an apparent ISI of the reagent.

Since suppression of the contact phase of the clotting cascade is critical for precise measurement of the tissue factor initiated thrombin generation the use of contact pathway inhibitors is necessary. The preferred method of achieving this end has been the addition of 50-100 mg/ml of CTI (a specific factor XIIa inhibitor) to whole blood samples immediately after phlebotomy. At these concentrations of CTI, the traditional APTT clotting time is extended 2-3 fold while the PT time is unaffected.

The CTI is titrated into the assay to establish the lowest level feasible in the assay. In a similar manner, we can use two other contact pathway inhibitors, aprotinin (a potent kallikrein inhibitor) and an inhibitory anti-human factor XI monoclonal antibody. Aprotinin is readily available in pharmaceutical grade preparations. We titrate aprotinin into whole blood prior to performing the tissue factor initiated thrombin generation assay. A similar analysis is performed using increasing concentrations of an anti-human factor XI monoclonal antibody which is a very potent inhibitor in APTT based clotting assays. In addition to using these inhibitors independently, they can be used in combination with each other. Significantly lower levels of CTI can be sufficient when used in combination with a Factor XI and/or kallikrein inhibitor.

EXAMPLE 1

Blood Collection Tube that Simplifies Generation of the Thrombin Generation Assay Relipidated tissue factor (5 nM TF, 10 mM 75PC:25PS), is co-lyophilized into glass blood collection tubes with corn trypsin inhibitor (CTI) (2.0 mg/mL) in the presence of 10% trehelose. Volumes are adjusted to yield final concentrations in whole blood of 5 pM functional tissue factor and 100 µ/mL CTI. Five test formulations of relipidated tissue factor and corn trypsin inhibitor, as outlined in the table below, were lyophillized into glass blood collection tubes.

| Formulation | Lipid Composition | Lipid Concentration (nM) | Nominal TF Concentration (pM) | Relipidation Procedure* |
|---|---|---|---|---|
| D1 | PC/PS: 75/25 | 25 | 12.5 | 1 |
| D2 | PC/PS: 75/25 | 25 | 12.5 | 1 |
| D3 | PC/PS: 75/25 | 25 | 12.5 | 1 |
| D4 | PC/PS/PG/PE | 25 | 12.5 | 2 |
| D5 | PC/PS/PG/PE | 700 | 12.5 | 2 |
| Control# | PC/PS 75/25 | 25 | 12.5 | 1 |

PC: phophatidylcholine;
PS: phosphatidylserine;
PG: phosphatidylglycerol;
PE: phosphatidylethanolamine
*The relipidation procedure is described in under "Reagents and Materials" in Section D.
Control utilizes TF preparation from the University of Vermont.

Whole phlebotomy blood was aliquoted (1 mL) into tubes D1-D5 (in triplicate, except for D3 and D4) and allowed to rock at 37° C. for 20 min. A control tube containing freshly prepared relipidated tissue factor (control) and corn trypsin inhibitor (100 µg/mL) was simultaneously tested. After 20 min, the tubes were quenched with a final concentration of 25 mM EDTA, 10 mM benzamidine and 50 mM FPRck. After quenching, serum was separated by centrifugation for 15 min at 1100×g, and then stored at −80° C. until analyzed.

Thrombin generation was determined by TAT ELISA assay. Results are presented in the table below.

| Formulations | TAT (nM) |
|---|---|
| D1 | 893.5 ± 14.6 |
| D2 | 877.8 ± 31.2 |
| D3 | 1038.4 |
| D4 | 926.9 |
| D5 | 834.6 ± 52.6 |
| Control | 853.6 ± 37.9 |

EXAMPLE 2

Manufacture of Blood Collection Tubes for Use in the Thrombin Generation Assay

Three lots are prepared. A portion of each lot are placed into controlled storage at 4° C., room temperature, and 37° C. for stability studies. Stability is assessed by functioning in the thrombin generation assay, in a plasma based PT clotting assay and in a functional tissue factor assay. Assays are run weekly for the first month, then monthly for the next 5 months. This invention encompasses optimizing the formulations by varying the following: changes in the excipient, changes in the lyophilization schedule, increasing amounts of reagent and changes in the relipidated tissue factor formulation.

EXAMPLE 3

Plasma-Based Thrombin Generation Assay

As an alternative to the whole blood thrombin generation assay, this assay is performed on plasma samples. A plasma based assay involves collecting blood into an evacuated blood collection tube containing sodium citrate and contact pathway inhibitors. The plasma sample derived from this tube is then assayed in a modified tissue factor initiated thrombin generation assay substituting plasma for whole blood and initiating with tissue factor in the presence of sufficient quantities of $CaCl_2$ or stored frozen for subsequent analysis at a more convenient time or place. The major change required is the recalcification of plasma when the relipidated tissue factor is added.

Blood is drawn into an evacuated blood collection tube containing sodium citrate (11 mM final) and CTI (100 mg/mL final) and plasma separated by centrifugation at 3000×g for 15 minutes. The blood collection tube is obtained commercially. The resultant plasma is aliquoted and frozen at −80° C. for future use.

Plasma samples are thawed at about 37° C. and supplemented with relipidated tissue factor (5 pM functional) and calcium chloride (10 mM). After rocking gently at 37° C. for 20 minutes, the reaction is quenched by addition of EDTA (25 mM), benzamidine (10 mM), and FPRck (50 mM). Serum is separated by centrifugation and the level of TAT is quantitated by ELISA.

EXAMPLE 4

Measurement of Thrombin Over Time for Thirteen Individuals

HEPES, Tris-HCl, EDTA, TFA, brain phosphatidyl serine (PS), egg phosphatidyl choline (PC) were purchased from Sigma Chemical Co (St. Louis, Mo.). Benzamidine-HCl was purchased from Aldrich, Inc (Milwaukee, Wis.). Recombinant tissue factor was relipidated in PCPS (25% PS, 75% PC) vesicles. Corn trypsin inhibitor (CTI) was prepared as described in U.S. Pat. No. 6,403,381. D-phenylalanyl-L-prolyl-L-arginine chloromethyl ketone (FPRck) and biotinylated FPRck were obtained from Haematologic Technologies, Essex Junction, Vt. An enzyme-linked immunosorbant assay (ELISA) was used to estimate thrombin-antithrombin-III (TAT) complex formation (Behring, Westwood, Mass.).

Thirteen healthy male subjects, mean age 35±13 years (range 22-60 years) were recruited and advised according to a protocol approved by the University of Vermont Human Studies Committee. All donors selected did not have a personal history of thrombosis/hemorrhage, regular aspirin, or drug use. Individuals were studied using the whole blood assay once a month (between 4-5 weeks) for six months, between 8:30 am and 1 pm. No specific limits were provided regarding diet or behavior. Coagulation profiles including, fibrinogen, antithrombin III, prothrombin, factor V, factor VII, factor VIII, factor IX, and factor X were performed by the Fletcher Allen Hematology Clinic of Burlington, Vt. (Table 2).

TABLE 2

Factor Levels of Subjects Studied over Six Months.

| Subject | AT III(%) | fII(%) | fV(%) | fVII(%) | fVIII(%) | fIX(%) | fX(%) | Fbgn (mg/dL) | Protime (s) |
|---|---|---|---|---|---|---|---|---|---|
| 1 | 129 | 110 | 96 | 91 | 55 | 144 | 114 | 411 | 13.6 |
| 2 | 94 | 99 | 90 | 78 | 70 | 82 | 107 | 220 | 13.8 |
| 3 | 116 | 125 | 115 | 108 | 206 | 109 | 114 | 238 | 12.3 |
| 4 | 112 | 96 | 131 | 98 | 99 | 88 | 97 | 246 | 12.7 |
| 5 | 90 | 106 | 86 | 81 | 118 | 116 | 93 | 380 | 12.9 |
| 6 | 104 | 84 | 97 | 78 | 146 | 86 | 91 | 274 | 14.6 |
| 7 | 115 | 114 | 92 | 99 | 67 | 101 | 132 | 250 | 13.3 |
| 8 | 72 | 93 | 74 | 88 | 96 | 71 | 86 | 198 | 14.1 |
| 9 | 104 | 92 | 77 | 78 | 126 | 69 | 85 | 164 | 14.1 |
| 10 | 114 | 87 | 85 | 81 | 77 | 51 | 85 | 174 | 12.8 |
| 11 | 111 | 96 | 83 | 101 | 80 | 79 | 88 | 242 | 13.0 |
| 12 | 116 | 78 | 87 | 87 | 77 | 80 | 99 | 203 | 13.0 |
| 13 | 95 | 78 | 77 | 59 | 170 | 67 | 72 | 290 | 14.1 |
| Normal[1] | 86–128 | 60–140 | 60–140 | 60–140 | 64–232 | 69–151 | 60–140 | 180–433 | 11.7–13.1 |

Blood was collected by venipuncture and aliquoted (about 1 mL) into tubes containing corn trypsin inhibitor (about 100 mg/mL) and tissue factor (functionally ~5 pM) relipidated in PCPS (about 1:2000 protein/lipid). The same stock of tissue factor and corn trypsin inhibitor were used for the duration of the 6 month study. A control tube containing corn trypsin inhibitor and no tissue factor was used for each experiment.

Blood containing tubes were allowed to rock at about 37° C. for 20 minutes (18 cycles/min) and then quenched 1:1 with a cocktail of inhibitors (50 mM EDTA and 20 mM benzamidine-HCl in HBS, pH 7.4 plus 10 mL of 10 mM FPRck in 10 mM HCl), the latter freshly prepared. Clot times were determined visually by two observers. After quenching, samples were centrifuged for about 15 min at about 2000 rpm and clot material separated from the solution phase. Solid and solution phases were stored at approximately −145° C. prior to further analysis. All samples collected during the 6 month study were stored until the completion period of the study and analyzed simultaneously.

Thrombin-antithrombin III (TAT), the integrator of thrombin, was determined using a commercial enzyme linked immunosorbant assay (ELISA) from Behring of Westwood, Mass. The limit of detection is 40 pM. A standard curve was generated using 4 concentrations of standards run in duplicate. Whole blood samples were diluted 1:1000 and run in duplicate. An optical density reading was obtained on a TMax microtiter plate reader equipped with SOFTMAX version 2.0 software made by Molecular Devices, Inc. of Menlo Park, Calif. Concentration results were obtained using a comparison to absorbance at 490 nm and fit to a four-parameter equation $(y=(A-D)/(1+(x/C)B)+D)$. Parameters A-D are determined by the SOFTMAX software from the generated standard curve.

Computationally generated active thrombin profiles are obtained utilizing a software package termed Speed RxClot Speed II. This model is composed of 10 reactants, the procoagulants tissue factor, factor VII/VIIa, factor IX, factor X, prothrombin, factor V and factor VIII, and the anticoagulants, tissue factor pathway inhibitor and antithrombin III. The combination of thirty four rate equations, 42 rate constants and 27 equilibrium expressions for the 10 reactants describe the processes of reagent consumption and product formation.

Figure 3:
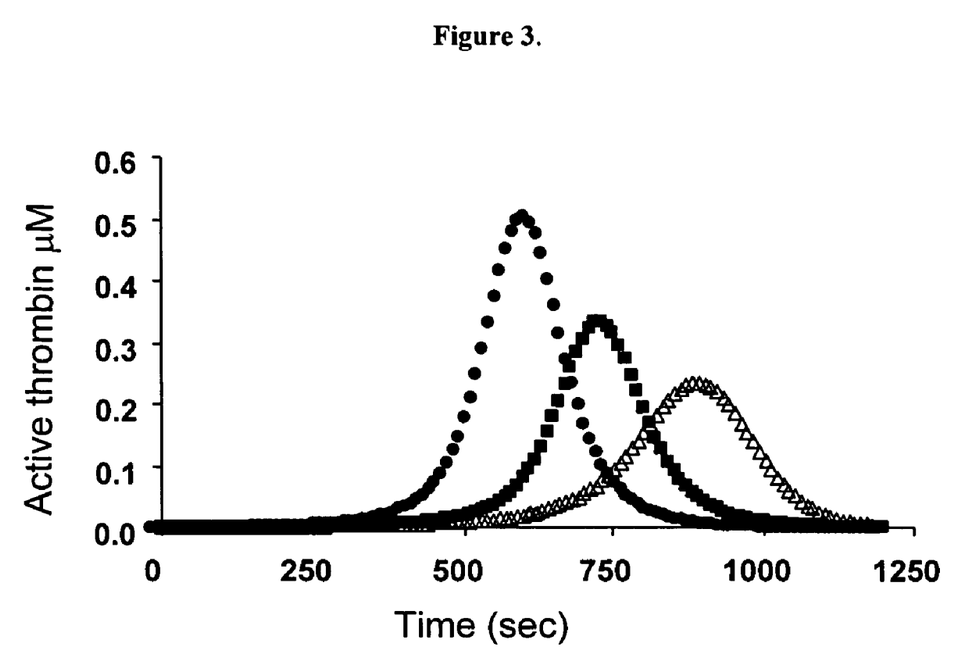
FIG. 3 shows computer simulation models for three individuals based upon factor analyses data obtained by a preferred embodiment of this invention.

Speed Rx utilizes an internet based interface with a generally applicable fourth order Runge-Kutta solver that provides solutions to a family of time-dependent differential equations. The procoagulant and anticoagulant levels for the 10 reactants were obtained for each individual and entered into the computer database, initiated with 5 pM tissue factor stimulus (same as whole blood stimulus) and solved for active thrombin (FIG. 3).

Analyses of variance (ANOVA) were performed on TAT generation (for n=13 subjects, mostly with 6 time points each, 72 samples) and CRP. The coefficient of variation (CV) was calculated for: analytical variation ($CV_a$), the square root of the mean variance ($SA^2$) for 72 samples divided by the mean value of the 72 samples×100; intra individual variation ($CV_i$), the square root of $SI^2$ divided by the mean value of the 72 samples×100; and inter-individual variation ($CV_g$) the square root of $SG^2$ divided by the mean value of the 72 samples×100.

The index of individuality, how individuals vary relative to the population distribution, was calculated as the ratio $CV_i/CV_g$. Correlations between TAT and CRP, age, antithrombin III, factors II, V, VII, VIII, IX and X, fibrinogen, protime, and clot time were evaluated using Spearman correlation and presented as r and p values. Pairwise t-tests and Wilcoxon rank sum tests were also performed between the cumulative 13 individual data and individuals on coumadin therapy, hemophilia A and B with and without replacement, factor XI deficiency and platelet IIbIIIa inhibitors and expressed as p-values.

Coagulation factor analyses for antithrombin III, factor II, factor V, factor VII, factor VIII, factor IX, factor X and fibrinogen for the thirteen individuals are shown in Table 2. The normal values reported by the Coagulation Laboratory at Fletcher Allen Health Care are shown at the bottom of the table. Subject 8 had low antithrombin III levels of 72% and subject 1 was on the high normal side with 129% (normal: 86-128%). Subject 13 was on the low normal side for factor VII with 59% (normal: 60-140%). Subject 1 had low factor VIII levels of 55% (normal: 64-232%). Subject 10 had low factor IX levels of 51% (normal: 69-151%). All subjects fell within normal values as indicated for factor II, factor V factor X and fibrinogen.

The visual clot times for the thirteen individuals over the course of 6 months are shown in Table 3. The mean and standard deviation for the whole population was 5.83±1.04 min. There was little variability between clot times and draw date, with subjects 3, 4 and 10 varying the most with clot times of 5.23±1.03, 5.35±1.03 and 6.04±1.45 min, respectively. Subject 9 consistently had long clot times of 7.63±0.92 min. A negative correlation was identified between an individual's clot time and ultimate thrombin levels (r=0.54, p=0.07).

TABLE 3

| | | | Clot times. | | | | |
|---|---|---|---|---|---|---|---|
| Subject | Month 1 | Month 2 | Month 3 | Month 4 | Month 5 | Month 6 | Mean ± SD |
| 1 | 4.17 | 5.85 | 5.77 | 6.12 | 6.03 | 6.81 | 5.79 ± 0.88 |
| 2 | 5.67 | N/D | 6.37 | N/D | 5.27 | N/D | 5.77 ± 0.56 |
| 3 | 4.75 | 4.83 | 6.15 | 5.92 | 3.57 | 6.17 | 5.23 ± 1.03 |
| 4 | 4.08 | 4.42 | 6.5 | 6.52 | 5.03 | 5.55 | 5.35 ± 1.03 |
| 5 | 5.67 | 6.18 | 6.3 | 6.53 | 6.48 | 5.28 | 6.07 ± 0.50 |
| 6 | 4.83 | 5.1 | 6.38 | N/D | 6.05 | 5.43 | 5.56 ± 0.65 |
| 7 | 8 | 6.15 | 7.92 | 5.88 | 7.1 | 6.27 | 6.89 ± 0.93 |
| 8 | N/D | 5.52 | 5.03 | 4.42 | 4.57 | 5.89 | 5.09 ± 0.62 |
| 9 | 6.83 | 7.0 | 8.02 | 9.05 | N/D | 7.23 | 7.63 ± 0.92 |
| 10 | 3.53 | 5.42 | 6.6 | 7.5 | 7.2 | 6.02 | 6.04 ± 1.45 |
| 11 | 5.97 | 6.75 | 5.42 | 4.93 | 5.68 | 5.44 | 5.70 ± 0.62 |
| 12 | 5.83 | 5.17 | 6.08 | 5.77 | 5.25 | 5.96 | 5.68 ± 0.38 |
| 13 | 4.33 | 5.0 | 4.95 | 6.2 | 6.02 | 4.41 | 5.15 ± 0.79 |

N/D: not determined

Six experiments were performed for blood collected from each of the 9 individuals. Blood was collected for subjects 6, 8 and 9 five out of six times and for subject 2 only three out of six times during the course of the study. Thrombin, expressed at TAT, was analyzed after all the samples were collected and at the same time with the same lot of ELISA plates (Table 1). The thrombin values encompass a broad range with a cumulative mean of 414.2±111.2 nM. Subject 9 and subject 10 had relatively low levels of thrombin as well as longer clot times (compare Tables 1 and 3). Subject 9 had a mean thrombin level of 401.6±31.1 nM and a mean clot time of 7.63±0.92 min. Subject 10 had a mean thrombin level of 270.6±19.6 nM and a mean clot time of 6.04±1.45 minutes.

Figure 1:
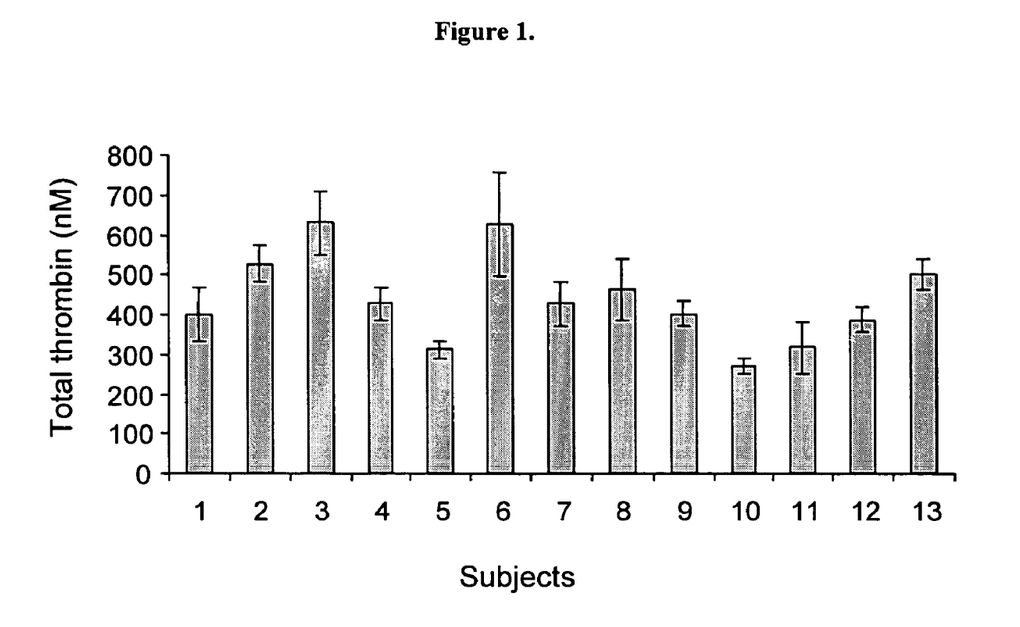
FIG. 1 shows one point measurement of thrombin levels for 13 non-diseased individuals. The data is shown as a bar graph of the mean±standard deviation for 6 months. This figure illustrates variation in a population that is observable with the use of the present invention. Subject 2 is the mean of only three times and subjects 6, 8 and 9 are the mean of five times.

The results show that there is a general propensity for any given individual to respond with a defined level of thrombin for a constant tissue factor stimulus. Levels range from 270.6±19.6 nM thrombin (subject 10) to 629.6±80.8 nM thrombin (subject 3). The mean values (±SD) for each individual are expressed in FIG. 1. FIG. 1 shows one point measurement of thrombin levels. Thrombin as assessed by thrombin—antithrombin III complex formation (TAT) for 13 healthy individuals are shown as a bar graph of the mean±standard deviation for 6 months. Subjects 1-13 are labeled below the appropriate bar. Subject 2 is the mean of only three times and subjects 6, 8 and 9 are the mean of five times.

Figure 2:
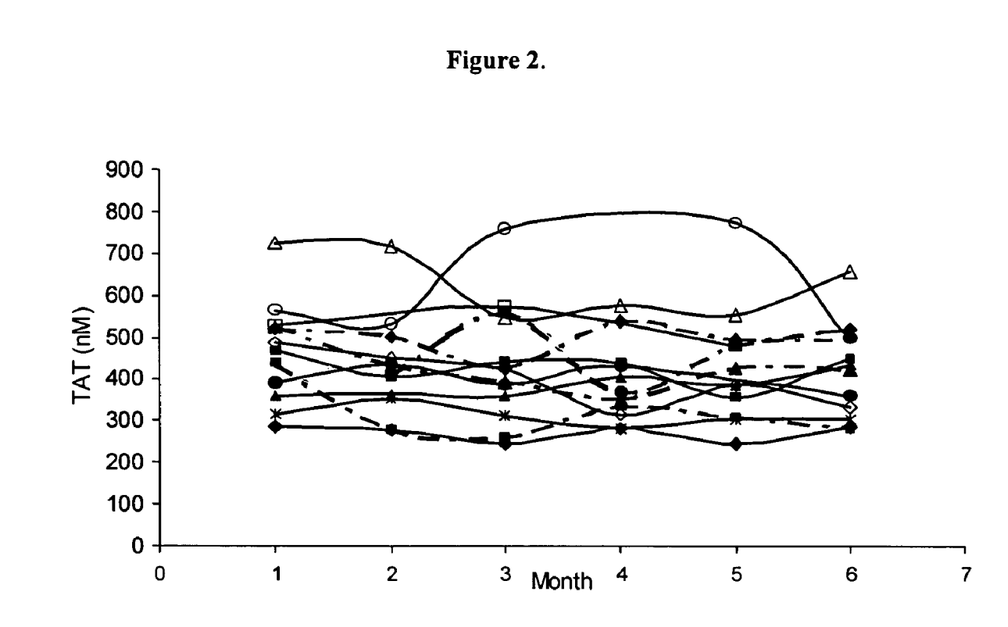
FIG. 2 shows thrombin data for 13 individuals over a six month time period obtained by a preferred embodiment of this invention. The data shows the relatively small variation observed by the assay for individuals over time.

The individual variations over the course of the study in thrombin levels are seen in FIG. 2. FIG. 2 shows six-month individual thrombin profiles. Thrombin generation as determined by thrombin—antithrombin III is illustrated for the 13 individuals over the course of a 6-month time period. Subject 1 ($\Diamond$), subject 2 ($\square$), subject 3 ($\Delta$), subject 4 ($\blacksquare$), subject 5 (*), subject 6 ($\circ$), subject 7 (dashed line $\blacktriangle$), subject 8 (dashed line $\bullet$), subject 9 ($\bullet$), subject 10 ($\blacklozenge$), subject 11 (dashed line $\blacksquare$), subject 12 ($\blacktriangle$), and subject 13 (dashed $\blacklozenge$). The mean thrombin level of the 13 healthy individuals was 414.2±111.2 nM. Subject 6 ($\circ$) and subject 3 ($\Delta$) varied the most having thrombin mean levels of 625.8±131.0 nM and 629.6±80.8 nM, respectively. The two subjects with the lowest levels of thrombin varied the least; 270.6±19.6 (subject 10, $\blacklozenge$) and 312.4±22.3 (subject 5, *).

ANOVA on the TAT data (Table 1) shows that our duplicate measurements using the TAT assay kit had an analytical variance $CV_a(\%)=7.02$. Individuals did not vary much within themselves $CV_i(\%)=11.63$. But individuals did vary from one to another $CV_g(\%)=25.20$. The index of individuality is mid range $(CV_i/CV_g)=0.461$.

A marker for inflammation, CRP, was evaluated in each individual over the course of the study. ANOVA results on CRP levels show an analytical variance of $CV_a(\%)=14.28$, and variability within an individual $CV_i(\%)=53.55$ and between individuals $CV_g(\%)=27.35$. The index of individuality is 1.96. Two of the subjects presented with a cold when blood was drawn and their CRP levels were increased for the draw. Subject 4, month 4 had a CRP=3.49 and subject 13 month 6, had a CRP=3.07 (normal values=0.75-1.0).

Correlation analyses between coagulation parameters and TAT levels for 12 participants with subject 6 removed were performed (data not shown). An inverse correlation was observed between clot time and TAT level (r=-0.54 and p=0.07). No significant correlations were observed between CRP, antithrombin III, factor II, factor V, factor VII, factor IX, factor X, factor VIII, fibrinogen and protime with TAT levels using a Spearman correlation.

The analyte levels for each of the thirteen individuals (values shown in Table 1) were used to develop a numerical analyses of each person's hemostatic response using the Speed Rx method. Active thrombin (mM) versus time (1200 secs) showed thrombin values ranging from 220 to 500 nM. Subject 3 ($\bullet$) had the highest whole blood thrombin generation TAT value of 629.6±80.8 nM and also showed the highest level of active thrombin of 500 nM using the numerical model.

This is shown in FIG. 3. FIG. 3 shows computer simulation of thrombin generation. Three individuals were modeled for active thrombin generation based upon their protein factor levels found in Table 1. Subject 3, 10, and 13 reflect the low, mid and high range of thrombin generation in the tissue factor based whole blood model (Table 1). Using a computer simulated model called Speed Rx (Clot Speed II), the same individual pattern of low mid and high thrombin generation was obtained. Subject 3 ($\bullet$) shows the highest thrombin levels of approximately 550 nM followed by subject 13 ($\blacksquare$) with approximately 350 nM and subject 10 ($\Delta$) with only 250 nM. The lowest thrombin generator, subject 10 ($\square$) with a TAT value of 270.6±19.6 nM, displayed a maximum active thrombin level of 220 nM in the numerical model. Subject 13 ($\blacksquare$), an individual with intermediate levels of thrombin generation, had TAT levels of 500.4±38.6 nM and predicted intermediate maximum active thrombin levels of approximately 350 nM.

During the tissue factor initiated whole blood reaction the duration of the initiation phase coincides with the clot time and the generation of 10 nM thrombin. The simulated active thrombin profiles for subject 3, subject 13 and subject 10 were evaluated for the time to form 10 nM thrombin. The calculated initiation phase for subject 3 was 320 seconds (5.3 min), followed by subject 13 at 460 seconds (7.7 min) and subject 10 at 530 seconds (8.8 min). The whole blood clot times were 5.23±1.03 min, 5.15±0.79 min and 6.04±1.45 min, respectively.

In the healthy population a wide range (approximately 200-800 nM) of thrombin was observed in a purely tissue factor initiated reaction. Low levels of thrombin (<200 nM) are evident in potential hemorrhagic situations. The absence of a propagation phase is correlated with hemorrhagic pathology. A group of healthy individuals was compared with an historical record of whole blood data for individuals on coumadin therapy, individuals with hemophilia A and B, individuals with and without replacement, individuals with factor XI deficiency at low tissue factor, and blood treated with anti platelet glycoprotein IIbIIIa therapeutics. These data, evaluated for the thrombin present at 20 minutes are compared in FIG. 4.

Figure 4:
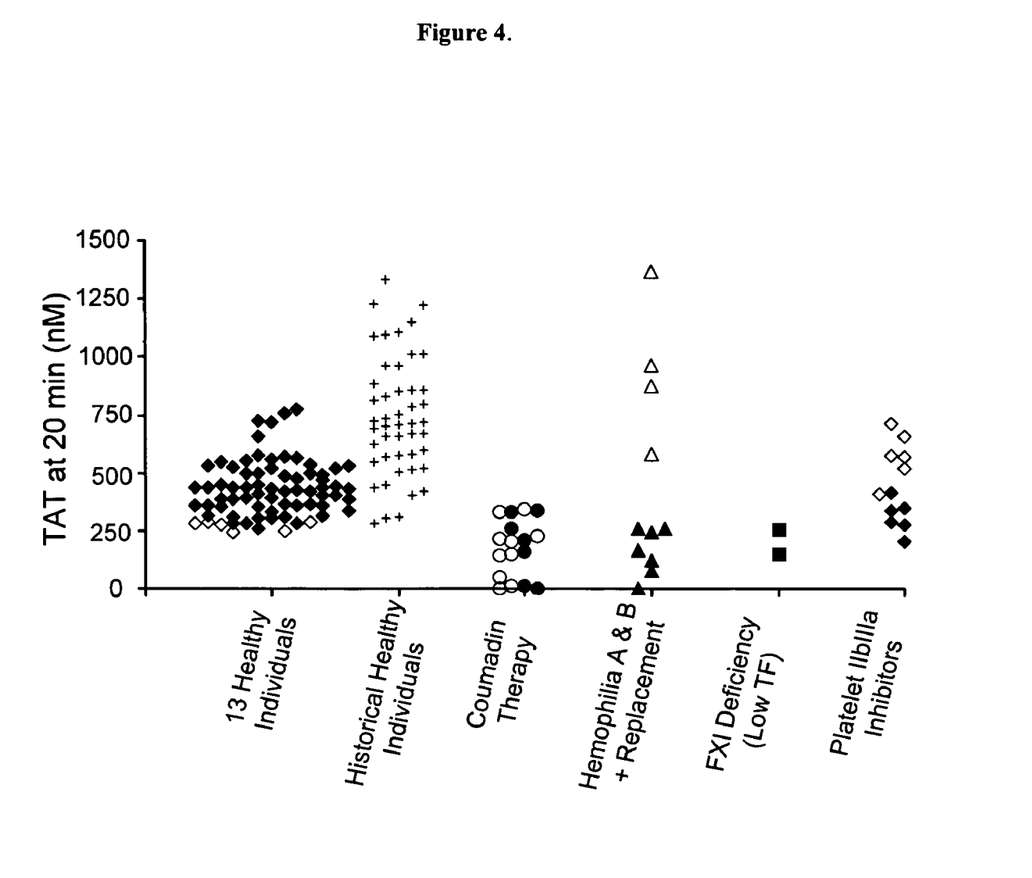
FIG. 4 compares a group of healthy individuals with an historical record of data for healthy individuals, individuals on coumadin therapy, individuals with hemophilia A and B, individuals with and without replacement, individuals with factor XI deficiency at low tissue factor, and blood before and after in vitro treatment with anti platelet glycoprotein IIbIIIa therapeutics.

FIG. 4 shows thrombin levels as an evaluator of an individual's hemostatic competence. Thrombin is illustrated for the group of 13 healthy individuals ($\blacklozenge/\Diamond$, column 1), with the 6-month time period for subject 10 ($\Diamond$) illustrated. In column 2, 48 experiments (+) from our historical controls (conducted over a 7 year time period) showed thrombin values ranging from approximately 280 to 1400 nM. An historical record of whole blood data for individuals on coumadin therapy ($\bullet/\circ$) is seen in column 3. One individual on coumadin therapy ($\circ$) was studied 10 times over the course of 6 months with a stable INR of 2.1±0.4. A group of 7 individuals ($\bullet$) stably anticoagulated on coumadin with an INR of 2.3±0.5 were studied once. Individuals with hemophilia A; or induced hemophilia B; with ($\Delta$) and without ($\blacktriangle$) in vitro replacement were reevaluated for their 20 minute time point and are seen in column 4. Two individuals with factor XI deficiency ($\blacksquare$) at low tissue factor are shown in column 5. Thrombin generation from blood treated with anti platelet IIbIIIa therapeutics (*), ReoPro and Integrellin are represented in column 6.

Seventy two blood draws were performed on the thirteen healthy volunteers (column 1, FIG. 4, ♦ and subject 10 ◇). Measurements display thrombin concentrations between 200 and 800 nM. The consistency of thrombin generation is seen in subject 10 (◇) with a 6-month mean of 270.6±9.6 nM. An individual on coumadin therapy stably anticoagulated (INR of 2.1±0.4) over a 6-month period (column 3, ○), varied from 0 to approximately 350 nM. A group of 7 individuals on coumadin therapy (INR of 2.3±0.5) studied once are presented (● column 3). In this column the shaded circles display thrombin levels also ranging from zero to approximately 350 nM. Thus a stable INR in one individual (○) over 6 months and in a group (●) studied once was not predictive of thrombin levels.

Disrupting the platelet glycoprotein IIbIIIa ligand interaction (in vitro) with either the inhibitors ReoPro (4 experiments, * column 5) and Integrelin (2 experiments, * column 5) show values that span the range to the normal healthy range of 200-400 nM thrombin.

The mean thrombin levels for the healthy controls were tested for differences between group means of individuals on coumadin therapy, hemophilia A and B with and without replacement, factor XI deficiency and platelet IIbIIIa inhibitors (Table 4). For all groups, any repeated measures on individuals were averaged so that each individual is represented only once in each group. Significant differences are seen between the healthy group and individuals on coumadin therapy (t-test p=0.001, Wilcoxon p=0.002), hemophilia A and B (t-test p=0.0008, Wilcoxon p=0.004) and hemophilia A and B replacement (t-test p=<0.0001, Wilcoxon p=0.01).

TABLE 4

Comparisons of TAT Level by Group. Mean TAT level for each group** and tests for differences between group means.

| | N | TAT level Mean | Std. Dev. | P-value for pairwise t-tests, each group vs. control group | P-value for Wilcoxon rank sum test |
|---|---|---|---|---|---|
| 1. Controls (6-Month Study) | 13 | 437.5 | 111.2 | ref | ref |
| 2. Coumadin | 8 | 273.5 | 60.1 | 0.001 | 0.002 |
| 3. Hemophilia A and B | 4 | 181.2 | 91.3 | 0.0008 | 0.004 |
| 4. Hemophiliacs + Replacement | 3 | 936.7 | 55.5 | <0.0001* | 0.01 |
| 4. Factor XI deficiency | 5 | 352.7 | 161.3 | 0.22 | 0.32 |
| 5. Platelet IIbIIIa inhibitors | 6 | 313.3 | 71.2 | 0.02 | 0.03 |

*Significant at 0.05 level when adjusted for multiple comparisons
**For all groups, any repeated measures on individuals were averaged so that each individual is represented only once in each group The best illustration of individual variation between a healthy state and on coumadin therapy during a six month time period is the comparison of subject 10 column 1 (◇) and the one individual in column 2 (○). The healthy individual had thrombin values varying only by 42 nM over 6 months, ranging from 246.5-288.0 nM (mean 270.6±19.6 nM thrombin). When compared to the one individual on coumadin therapy (○) thrombin levels varied approximately 325 nM with a range from 9.3-334.7 nM (mean 166.6±121.3 nM thrombin) over a 6 month time period. The scatter in the thrombin levels of the individual on stable coumadin therapy potentially reflects an on-going hemostatic tissue factor challenge compared to the healthy individual.

The genotype for hemophilia suggests a bleeding phenotype, but when four hemophilia A and B individuals were studied (7 experiments total, ▲ column 3) thrombin levels at 20 minutes ranged from approximately 0-250 nM TAT. These values indicate that at different times within an individual and between hemophiliac individuals the propensity to generate thrombin is not the same. In fact the higher thrombin concentrations observed in hemophilia fall within the healthy range. With replacement of either factor VIII or factor IX in vitro thrombin levels dramatically increased to a range of 600-1400 nM (Δ, column 3). These numbers approximate and exceed values observed in the healthy population. When two factor XI deficient individuals, hemophilia C, are investigated at low tissue factor concentrations (■, column 4), thrombin levels were in the lower range of approximately 150 and 250 nM TAT.

The data indicate that thrombin levels are individual specific in a tissue factor initiated whole blood analyses of hemostatic potential. The test utilized is a modification of whole blood tissue factor studies which have examined thrombin generation, fibrin formation and platelet activation for healthy and hemostatically compromised individuals. This model has been modified to be a simple to perform one point measurement to allow us to develop an evaluation of thrombin generating potential. The advantage of this method compared to others is that thrombin is generated in native blood with all cellular constituents present, no dilution, no anticoagulation, no temperature change and no detecting substrate (inhibitor) to alter the outcome.

In the healthy population studies thrombin at 20 min ranged from approximately 200-800 nM (FIG. 2). The low analytical ($CV_a$), individual ($CV_i$) and large population variability ($CV_g$) characteristics of the assay (Table 3) make this assay a good diagnostic test.

The potential utility of a hemostatic monitoring assay is evaluated by several criteria including: ease of sample collection, assay variability, consistency of the measured marker within an individual, analyte concentration range between individuals in a population, and the strength of the association of the measured marker to an outcome. For example, fibrinogen measured by a clotting assay has low analytical variance ($CV_a$=1.6%) and individuals do not vary significantly between themselves ($CV_i$=18.6%) as well as within a population ($CV_g$=20.2%). In comparison, cholesterol, a well established cardiovascular disease risk factor, has assay variability ($CV_a$) of only 1%, and intra ($CV_i$) and inter ($CV_g$) individual variability of 8.8% and 19.8%, respectively.

The power of a four fold range in thrombin production in the "healthy" population allows for a sufficient value span for determining the strength of the association of thrombin levels to an outcome. When evaluated at the 20 min thrombin level (FIG. 4) the historical data predicted a difference between healthy individuals and individuals on coumadin therapy (p=0.002), hemophiliacs with (p<0.01) and without replacement (p=0.004) and individuals receiving anti platelet glycoprotein IIbIIIa inhibitors (p=0.03) (Table 4). The range of thrombin in these pathology studies extended from zero to overlap with and exceeding the "healthy" group.

The computer analysis, Speed Rx used to integrate the factor levels in the healthy subject population predicted the order of low, mid and high thrombin generation of the appropriate individuals (FIG. 3). No one coagulation factor concentration dominated the outcome. The only significant correlation with thrombin was clotting time. Thus, there is a need for composite, integrated analyses to predict the propensity to respond of an individuals' blood to tissue factor.

The invention has been described with reference to preferred embodiments thereof. However, it will be appreciated that those skilled in the art, upon consideration of this disclosure, may make modifications and improvements within the spirit and scope of the invention. The disclosure of the following reference is hereby incorporated by reference.

Jenny N. S., Mann K. G. Coagulation Cascade: An Overview. In: Loscalzo J, Schafer A I, eds. Thrombosis and Hemorrhage. Baltimore: Williams & Wilkins; 1998:3-27.

What is claimed is:

1. A method for determining hemostatic competence of blood comprising,
   obtaining a blood sample from a subject,
   contacting the blood sample with an effective amount of tissue factor to coagulate the blood, under conditions conducive to coagulating blood; and
   determining an amount of thrombin in the blood sample at a pre-determined time point;
   wherein the amount of thrombin is indicative of the hemostatic competence.

2. The method of claim 1 wherein said tissue factor is phospholipid treated Tissue Factor.

3. The method of claim 1 wherein intrinsic coagulation in the blood sample is inhibited.

4. The method of claim 1 wherein the amount of thrombin is determined at a time that is less than about 100 minutes after contacting the blood sample with an effective amount of tissue factor, and thrombin production is complete in healthy subjects.

5. The method of claim 1 wherein the amount of thrombin is determined at a time that is between about 0.5 minutes and about 50 minutes after contacting the blood sample with an effective amount of tissue factor, and thrombin production is complete in healthy subjects.

6. The method of claim 1 wherein the amount of thrombin is determined at a time that is between about 5 minutes and about 25 minutes after contacting the blood sample with an effective amount of tissue factor, and thrombin production is complete in healthy subjects.

7. The method of claim 1 wherein the blood sample is further contacted with corn trypsin inhibitor or an active fragment thereof.

8. The method of claim 1 wherein the thrombin is determined by an immunological assay.

9. The method of claim 1 wherein the thrombin is determined by enzyme-linked immunosorbant assay.

10. The method of claim 1 wherein the thrombin is determined by Western blot.

11. The method of claim 1 wherein the thrombin is determined by radioimmunological assay.

12. The method of claim 1 wherein the amount of thrombin is determined at a time that is less than about 100 minutes after contacting the blood sample with an effective amount of tissue factor.

13. The method of claim 1 wherein the amount of thrombin is determined at a time that is between about 0.5 minutes and about 50 minutes after contacting the blood sample with an effective amount of tissue factor.

14. The method of claim 1 wherein the amount of thrombin is determined at a time that is between about 5 and about 25 minutes after contacting the blood sample with an effective amount of tissue factor.

15. The method of claim 1 wherein the thrombin is further contacted with an antibody, wherein the antibody specifically binds thrombin.

16. The method of claim 15 wherein the thrombin forms a complex comprising the antibody.

17. The method of claim 16, wherein the complex is thrombin-antithrombin (TAT) complex.

18. The method of claim 1 wherein, at the pre-determined time point, the sample is quenched with inhibitors in order to stop thrombin production.

19. The method of claim 18 wherein the inhibitors are Ethylenediaminetetraacetic acid, benzamidine-HCl in HBS (HEPES buffered saline), and D-phenylalanyl-L-prolyl-L-arginine chloromethyl ketone (FPRck) in HCl.

20. A method for testing capacity of an individual subject to produce thrombin comprising,
    obtaining a blood sample from the subject;
    contacting the blood sample with an effective amount of tissue factor to coagulate the blood, under conditions conducive to coagulating blood; and
    determining an amount of thrombin produced in the blood sample at a pre-determined time point;
    wherein the amount of thrombin is indicative of the capacity of an individual subject to produce thrombin.

21. A method for determining hemostatic competence of blood comprising the steps of,
    preparing an evacuated blood collection tube which contains a lyophilized preparation of intrinsic contact pathway inhibitor and tissue factor;
    obtaining a blood sample from a subject,
    contacting the blood sample with the lyophilized preparation, under conditions conducive to coagulating blood; and
    determining an amount of thrombin in the blood sample at a pre-determined time point;
    wherein the amount of thrombin is indicative of the hemostatic competetence.

22. The method of claim 21 wherein the inhibitor is corn trypsin inhibitor.

23. The method of claim 21 wherein the tissue factor is phospholipid treated Tissue Factor.

24. The method of claim 21 further comprising the step of quenching, in order to stop thrombin production, with EDTA, benzamidine, and FPRck.

25. A method for determining hemostatic competence of blood by a plasma based assay comprising, collecting a blood sample from a subject into an evacuated blood collection tube containing sodium citrate and intrinsic contact pathway inhibitors, contacting the blood sample with an effective amount of tissue factor to coagulate the blood, under conditions conducive to coagulating blood; and determining an amount of thrombin in the blood sample at a pre-determined time point;

wherein the amount of thrombin is indicative of the hemostatic competetence.

26. The method of claim 25 further comprising the step of adding relipidated tissue factor and calcium chloride to the sample.

27. The method of claim 26 further comprising the step of quenching, in order to stop thrombin production, with EDTA, benzamidine, and FPRck.

28. The method of claim 25 wherein the intrinsic contact pathway inhibitor is corn trypsin inhibitor.

* * * * *